United States Patent [19]

McCaleb

[11] Patent Number: 4,910,019
[45] Date of Patent: Mar. 20, 1990

[54] OXATHIADIAZOLE GROWTH PROMOTERS

[75] Inventor: Michael L. McCaleb, Plainsboro, N.J.

[73] Assignee: American Home Products Corporation, New York, N.Y.

[21] Appl. No.: 362,550

[22] Filed: Jun. 7, 1989

[51] Int. Cl.$^4$ .............................................. A61D 7/00
[52] U.S. Cl. .................................... 424/442; 424/439; 514/360; 514/352; 426/2; 548/122
[58] Field of Search ................ 424/442, 439; 514/360, 514/352; 426/2; 548/122

[56]  References Cited

U.S. PATENT DOCUMENTS 3,290,302  12/1966  Eloy ...................................... 548/122
4,761,421   8/1988  Muir ...................................... 514/352

OTHER PUBLICATIONS

Goodman & Gilman, the Pharmacological Basis of Therapeutics 6th Edition, 1980, chapters 32 and 36.

Primary Examiner—Thurman K. Page
Assistant Examiner—Shelly J. Guest
Attorney, Agent, or Firm—Richard K. Jackson

[57]  ABSTRACT

The compounds:

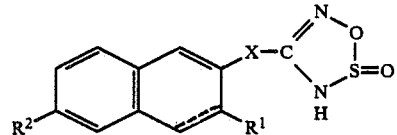

in which the dotted line represents optional unsaturation; $R^1$ is hydrogen, halo or alkoxy; $R^2$ is hydrogen or alkoxy and X is methylene, ethylene, ethylidene, 1,2-propylene or propylene; or a biologically acceptable salt thereof are growth promoting agents which rapidly lead to increased lean body mass in domestic animals and humans.

10 Claims, No Drawings

OXATHIADIAZOLE GROWTH PROMOTERS

DESCRIPTION OF THE INVENTION

In accordance with this invention, there is provided animal feed compositions containing a growth promoting amount of a compound of the formula:

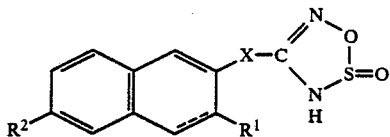

in which
the dotted line represents optional unsaturation;
$R^1$ is hydrogen, halo or alkoxy of 1 to 3 carbon atoms;
$R^2$ is hydrogen or alkoxy of 1 to 3 carbon atoms and
X is methylene, ethylene, ethylidene, 1,2-propylene or propylene; or a biologically acceptable salt thereof.

The most preferred growth promoters are those which increase the lean body weight gain of the standard experimental animal in the test procedure discussed infra by 60% or more during the test period, which compounds are the (3-methoxy- or 3-bromo-2-naphthalenyl)methyl derivatives, the (2-naphthalenyl)-1-methylethyl derivative and the (3,4-dihydro-2-naphthalenyl)methyl derivative embraced by the generic formula supra.

The salts of the growth promoters of this invention are those conventionally employed in foodstuffs and pharmaceutical compositions such as the sodium, potassium, calcium, magnesium salts. By biologically acceptable, applicant means pharmaceutically acceptable for human consumption and nutritionally suitable for incorporation in animal feeds.

The growth promoting property of the compounds disclosed herein was established by feeding male mice (Swiss CD-1 of 20 to 30 grams weight) by oral gavage either 0.2 milliliters of vehicle (2% Tween 80 ®/saline, w/v) or 50 mg/kg per day of the compound being tested in the same vehicle. This dosing regimen was repeated for four days, during which time the animals were provided ad libitum access to food. On the morning of the fith day, the animals were individually weighed and their weight change from day 1 was determined and the four day change as a percent of the vehicle control group was calculated. The results of this standard test procedure are presented for each specific compound at the end of the preparation examples, infra. While all of the compounds disclosed herein increased body weight gain of the standard experimental animal by at least 40%, the most active compound prepared in Example 6 actually increased the animals' weight gain by 120 percent (1.5 gram weight increase by vehicle control and a 3.3 gram weight gain with test compound). In all of these animals, it was apparent upon palpation that the weight gains were of lean body mass. Hence, these oxathiadiazoles are useful growth promoters for use as food supplements for mammals to increase their body protein content or as an oral medicament for treatment of human conditions involving excessive protein catabolism, such as septic shock, diabetes, uremia, etc.

The growth promoters of this invention may be incorporated into conventional food compositions, whether solid or liquid, for ad libitum presentation to the animals or into special food supplements such as conventional sweet feeds or the special sweet feeds disclosed in U.S. Pat. No. 3,895,117 or into conventional milk replacer. The optimum quantity of these growth promoters to be fed varies with the animal species and the nutritional goal, e.g. lean beef production will need larger quantities of promoter than veal production. Similarly growth promotion in animals being rapidly finished for market may be quite different from that desired for stock animals. In the human, the dose must be personalized for the patient by the attending physician.

In general, based upon the results obtained in animal testing, the amount of growth promoter to be used in initiating a program is about 10 mg/kg/day with increased dosing in relationship to the desired lean body mass increase and shorter time schedules for achieving market weights.

The growth promoting agents of this invention have little or no odor which can affect the palatability of the animal feed compositions or flavor their meat or milk adversely. No toxicity has been observed with the growth promoters of this invention which would be contraindicative of their prolonged use in ruminant and monogastric animals.

Compositions for human use will incorporate from about 50 milligrams to about 1 gram of the active growth promoter in unit dosage form with conventional carriers or diluents. For meat production, the compositions will be formulated to provide from about 1 mg/kg/day to about 100 mg/kg/day depending upon the animal involved and production rate desired. The carrier or diluent employed with the growth promoter additive is generally any material used as fodder in feeding animals, e.g. wheat, rice, maize, soybean, alfalfa, lespedeza, clover, barley, oats and rye can be used in appropriate form such as meal, groats, bran, grits or as untreated foodstuffs. Fish meal, meat meal, bonemeal or mixtures thereof are excellent carriers. Some excellent fodders to which the growth promoters of this invention may be added in an appropriate quantity are disclosed in U.S. Pat. No. 4,570,002.

Applicant does not know by what mechanism the growth promoters disclosed here operate and does not want to be bound by any specific theory of action, but because the weight increase observed in the standard experimental animal is lean body mass, it may be assumed that improved nitrogen utilization in production of protein is involved.

The growth promoters of this invention may be produced by the following procedures:

EXAMPLE 1

4-[(3,4-Dihydro-2-naphthalenyl)methyl]-3H-1,2,3,5-oxathiadiazole-2-oxide

Diethyl cyanomethylphosphonate (33.13 g, 0.187 mol was added dropwise to sodium hydride (8.98 g, 0.187 mol) in 400 ml of dry tetrahydrofuran. The reaction mixture was stirred at room temperature for half an hour, at which time β-tetralone (24.8 g, 0.170 mol) in tetrahydrofuran was added dropwise at 0° C. The reaction mixture was stirred at room temperature for one hour. Deionized water (600 ml) was added and the reaction mixture was extracted with diethyl ether (3×400 ml). The organic phase was washed with brine, dried over MgSO₄ and concentrated under reduced pressure to give 2-(3,4-dihydro)naphthalenylacetonitrile as an orange oil. High vacuum distillation provided 22.65 g (79% yield) of pure product.

Powdered hydroxylamine hydrochloride (8.27 g, 0.119 mol) was added to a solution of sodium methoxide (24.69 ml, 0.108 mol) in methanol (135 ml) and the mixture was refluxed for one-half hour. 2-(3,4-Dihydro)-naphthalenylacetonitrile (9.14 g, 0.054 mol) in methanol (42 ml) was added and refluxing was continued overnight. The solvent was removed under reduced pressure and the solid residue was diluted with deionized water (120 ml). The mixture was extracted with diethyl ether and the combined extracts were dried over $MgSO_4$ and concentrated under reduced pressure to give N'-hydroxy-(3,4-dihydro-2-naphthalenyl)ethanimidamide as a frothy oil. Purification by flash chromatography (9×10 cm silica gel column, 3% methanol/dichloromethane) gave 6.7 g (61.1% yield) of product.

Thionyl chloride (2.55 ml, 0.035 mol) was added dropwise to a mixture of N'-hydroxy-(3,4-dihydro-2-naphthalenyl)ethanimidamide (6.5 g, 0.032 mol) and pyridine (5.18 ml, 0.064 mol) in dry dichloromethane (100 ml) at 0° C. Upon completion of the addition, the reaction mixture was concentrated under reduced pressure, placed in an ice bath, diluted with deionized water (50 ml), extracted with diethyl ether (3×50 ml), filtered, dried over $MgSO_4$ and concentrated under reduced pressure to give the crude title compound as a red-brown solid. The solid was triturated with diethyl ether (3×50 ml), dissolved in boiling diethyl ether (100 ml), vacuum filtered and recrystallized from diethyl ether (75 ml) to yield 1.14 g (14.4% yield) of pure product, m.p. 118°-120.5° C.

Elemental analysis for $C_{12}H_{12}N_2O_2S$; Calc'd: C, 58.04; H, 4.87; N, 11.28; Found: C, 58.00; H, 5.20; N, 11.21.

Body weight increase over control: 61%.

EXAMPLE 2

4-[1-(2-Naphthalenyl)ethyl]-3H-1,2,3,5-oxathiadiazole-2-oxide

A solution of 2-naphthalenylacetonitrile (75 mmol, 12.5 g) and methyl iodide (75 mmol, 10.65 g, 4.67 ml) in a 1,2-dimethoxy ethane (75 ml) was added dropwise over a one hour period to a refluxing suspension of sodium hydride (75 mmol, 3.00 g, 60% dispersion in oil) in 1,2-dimethoxyethane (150 ml). The resulting dark solution was refluxed for three hours and cooled to room temperature. The 1,2-dimethoxyethane was removed in vacuo, the residue dissolved in diethyl ether (200 ml) and partitioned with water (150 ml). The layers were separated, the aqueous phase washed with diethyl ether (2×200 ml) and the organic extracts were combined, dried over $MgSO_4$ and concentrated in vacuo to give a mixture of α-methyl-2-naphthalenylacetonitrile and α,α-dimethyl-2-naphthalenylacetonitrile as a dark oil. The crude product was purified by preparative high pressure liquid chromatography ($SiO_2$:gradient elution with hexane/ethyl acetate) to initially give 2.28 g of the dimethyl compound as a light yellow oil and later the mono-methyl compound (5.68 g) which crystallized as a white solid.

The monomethyl compound (5.07 g) was converted to the N'-hydroxy-2-(naphthalen-2-yl)propanimidamide following the procedure of Example 1, with hydroxylamine hydrochloride and sodium ethoxide at reflux for three days. The product (4.18 g) was converted to the oxathiadiazole-2-oxide following the procedure of Example 1. The addition of thionyl chloride to the propanimidamide was performed at 0° C. over a thirty minute period. The crude product was purified by flash chromatography through a silica gel column employing dichloromethane, 0.5% ethyl acetate/dichloromethane, 1% ethyl acetate and 2% ethyl acetate serial elution solvents. The product is a light yellow oil.

Elemental analysis for $C_{13}H_{12}N_2O_2S.0.025CCl_4$; Calc'd: C, 59.22; H, 4.58; N, 10.61; Found: C, 59.30; H, 4.74; N, 10.24.

Body weight increase over control: 47%.

EXAMPLE 3

4-[1-Methyl-2-(2-naphthalenyl)ethyl]-3H-1,2,3,5-oxathiadiazole-2-oxide

To a stirred solution of naphth-2-ylpropionitrile (25 mmol, 4.52 g) in dry tetrahydrofuran (250 ml) at −78° C. was added n-butyl lithium (30 mmol, 18.75 ml; 1.6M solution in hexane) dropwise over a twenty minute period. After stirring the solution for twenty minutes at −78° C. methyl iodide (30 mmol, 4.26 g) was added in one portion. The reaction mixture was stirred for twenty minutes at −78° C. and the reaction was quenched with saturated $NH_4Cl$ (35 ml). The reaction mixture was warmed to room temperature, the volatiles were removed in vacuo, the residue diluted with water (200 ml) and extracted with diethyl ether (2×250 ml). The organic phase was washed with water (250 ml), dried over $MgSO_4$ and concentrated in vacuo. The crude product was purified by preparative high pressure liquid chromatography ($SiO_2$:hexane/dichloromethane) to give α-methyl-naphth-2-ylpropionitrile as a white solid (3.21 g, 66 percent of theory).

Following the procedure of Example 1, the α-methyl-propionitrile prepared in the preceding paragraph was refluxed with hydroxylamine hydrochloride and sodium methoxide in methanol for five days to give N'-hydroxy-2-methyl-3-(2-naphthalenyl)propanimidamide which was cyclized to the title compound following the procedure of Example 1. The crude product was purified by flash chromatography ($SiO_2$:dichloromethane) to yield a light yellow oil.

Elemental analysis for $C_{14}H_{14}N_2O_2S$; Calc'd: C, 61.29; H, 5.14; N, 10.21; Found: C, 60.94; H, 5.04; N, 10.08.

Body weight increase over control: 60%.

EXAMPLE 4

4-[3-(2-naphthalenyl)propyl]-3H-1,2,3,5-oxathiadiazole-2-oxide

To a stirred solution of 2-(2-hydroxyethyl)naphthalene (50 mmol, 8.60 g) in dichloromethane (400 ml) at 0° C. was added Dess-Martin periodinate (50 mmol, 21.2 g) [J. Org. Chem. 48 4155 (1983)] in one portion. The solution was stirred at 0° C. for 10 mintes and at room temperature for 45 minutes. The reaction mixture was diluted with dichloromethane (400 ml) and sodium bicarbonate (1.0 L) containing sodium thiosulfate (55 g). The mixture was shaken for five minutes and the layers separated. The aqueous phase was extracted with dichloromethane (800 ml) and the combined organic solutions were washed with saturated sodium bicarbonate (800 ml), dried over sodium sulfate and concentrated in vacuo to provide naphthalen-2-ylacetaldehyde.

To a stirred suspension of NaH (75 mmol, 3.00 g; 60% dispersion) in dry tetrahydrofuran (350 ml) was added diethyl cyanomethylphosphonate (55 mmol, 9.74 g) in tetrahydrofuran (75 ml) dropwise at 0° C. over 40 minutes. After stirring the solution at 0° C. for 10 minutes, naphthalen-2-ylacetaldehyde (50 mmol, 8.50 g) in tetrahydrofuran (75 ml) was added dropwise at 0° C. over 70 minutes. The resulting dark brown solution was stirred at 0° C. for 30 minutes and quenched with water (100 ml). The volatiles were removed in vacuo, the residue diluted with water (400 ml) and extracted with diethyl ether (2×400 ml). The organic phase was dried over MgSO$_4$ and concentrated in vacuo to provide a dark oil which was purified by preparative high pressure liquid chromatography (SiO$_2$: gradient hexane/dichloromethane) to give 4-(2-naphthalenyl)but-2-enylnitrile as a yellow solid (1.36 g).

The unsaturated nitrile produced in the preceding paragraph (7.0 mmol, 1.35 g) was catalytically hydrogenated in absolute ethanol (70 ml) with 5% palladium on carbon (135 mg) at 50 pounds per square inch hydrogen pressure for 45 minutes. The reaction mixture was filtered and concentrated in vacuo to give (4-(2-naphthalenyl)butyronitrile (1.34 g).

Following the procedure of Example 1, the nitrile produced in the preceding paragraph was refluxed with hydroxylamine hydrochloride and sodium methoxide in methanol for five days to obtain N'-hydroxy-(2-naphthalenyl)butanimidamide which was purified by flash chromatography (SiO$_2$: sequential dichloromethane followed by 4% methanol in dichloromethane).

Following the procedure of Example 1, the butanimidamide derivative produced in the preceding paragraph was converted to the oxathiadiazole-2-oxide with thionyl chloride. The product was triturated with dichloromethane to yield an analytically pure sample of the title compound as a white solid in 58 percent yield, m.p. 139°–140° C.

Elemental analysis for C$_{14}$H$_{14}$N$_2$O$_2$S; Calc'd: C, 61.29; H, 5.14; N, 10.21; Found: C, 60.91; H, 4.99; N, 10.22.

Body weight increase over control: 40%.

EXAMPLE 5

4-[(3-Bromo-2-naphthalenyl)methyl]-3H-1,2,3,5-oxathiadiazole

PBr$_3$ (3.7 mL, 0.039 mol) was added dropwise to a suspension of 3-bromo-2-naphthalenyl methanol (8.55 g, 0.036 mol) and diethyl ether (80 mL) at 0° C. After 1 hour, the reaction was concentrated and partitioned between CH$_2$Cl$_2$ and H$_2$O. The organic layer was separated and dried over MgSO$_4$. Concentration in vacuo afforded 3-bromo-2-bromomethylnaphthalene as a crude product (10.6 g). The crude product was flash chromatographed on silica gel to afford the pure product as an off-white powder (6.0 g, m.p. 110°–111° C., yield 56%).

A suspension of 3-bromo-2-bromomethylnaphthalene (6.0 g, 0.020 mol), DMSO (150 mL) and sodium cyanide (1.0 g, 0.020 mol) was stirred for 2 hours at room temperature. The resulting solution was added to ice/H$_2$O and extracted well with ethyl acetate. The organic phase was dried over MgSO$_4$, concentrated and dried in vacuo for 16 hours. Treatment of the resulting solid with diethyl ether/hexane afforded 3-bromo-2-naphthalenylacetonitrile (3.6 g), m.p. 116°–117° C.

The nitrile prepared in the preceding paragraph (3.59 g, 0.145 mol) was added to a slurry of hydroxylamine.HCl (1.69 g, 0.024 mol), methanol (15 mL) and 25% NaOCH$_3$/MeOH (5.7 mL, 0.024 mol) and then brought to reflux for 3 hours. The reaction was concentrated and ethyl acetate and water were added. The organic layer was separated, dried over MgSO$_4$ and concentrated in vacuo. The resulting solid was triturated with hexane to give N'-hydroxy-(3-bromo-2-naphthalenyl)ethanimidamide (3.3 g).

Thionyl chloride (2.0M/CH$_2$Cl$_2$; 7.4 mL, 0.015 mol) was added dropwise to a stirred suspension of N'-hydroxy-(3-bromo-2-naphthalenyl)ethanimidamide (3.29 g, 0.012 mol), methylene chloride (125 mL) and pyridine (2.4 mL, 0.03 mol) at 5° C. After 20 minutes at −5° C., the reaction solution was added to ice/H$_2$O. The organic layer was separated, washed with saturated NaCl, dried over MgSO$_4$ and concentrated in vacuo to a slurry (20 mL). Diethyl ether (20 mL) was added and the title compound (1.40 g, yield 36%) was collected (153°–154° C. decomp.).

Elemental analysis for C$_{12}$H$_9$BrN$_2$O$_2$S; Calc'd; C, 44.32; H, 2.79; N, 8.61; Found: C, 44.21; H, 2.96; N, 8.37.

Body weight increase over control: 67%.

EXAMPLE 6

4-[(3-methoxy-2-naphthalenyl)methyl]-3H-1,2,3,5-oxathiadiazole-2-oxide

A solution of 2-hydroxy-3-naphthoic acid (25.0 g, 133 mmol) in anhydrous tetrahydrofuran (THF) (200 mL) at 0° C., was treated with lithium aluminum hydride (1M solution in THF, 160 mL, 160 mmol) added dropwise over 1 hour. After the addition was complete, the ice bath was removed and the mixture was stirred at room temperature for 2.5 hours. More lithium aluminum hydride was added at 2 hour intervals (20 ml, 20 mmol, and 25 mL, 25 mmol) at room temperature. After a total of 2.5 days at room temperature, thin layer chromatography indicated the presence of starting material, therefore the mixture was heated to reflux for 10 hours. The mixture was cooled to 0° C. and quenched by cautious addition of ethyl acetate (50 mL), followed by water (50 mL). The orange mixture was poured over 500 mL 2N HCl/ice to give a white precipitate which was collected by filtration, washed with water and dried in vacuo. The product, 3-hydroxy-2-naphthalenylmethanol (16.4 g, 71%), was of sufficient purity for use in the subsequent reaction.

A solution of the diol prepared in the preceding paragraph (12.0 g, 69.0 mmol), triethylamine (9.06 g, 89.7 mmol), and t-butyldimethylsilyl chloride (12.5 g, 82.8 mmol) in CH$_2$Cl$_2$ (250 mL) was treated with a catalytic amount of dimethylaminopyridine (0.84 g, 6.90 mmol). The resulting mixture was stirred at room temperature for 2.5 hours, then diluted with water. The layers were separated and the aqueous layer extracted with CH$_2$Cl$_2$ (100 mL). The combined organic layers were washed with water (2×250 mL), brine, dried over anhydrous sodium sulfate and concentrated in vacuo to give a yellow oil (14.8 g).

Flash chromatography on silica gel with elution by ethyl acetate/hexane (5:95) gave the desired silyl ether, 2-tertiary-butyl-dimethylsilyloxymethyl-3-hydroxynaphthalene (9.5 g, 48%), as a yellow crystalline solid.

The silyl ether prepared in the preceding paragraph (9.0 g, 31.25 mmol) was added portionwise to a suspension of sodium hydride (60% dispersion, 1.5 g, 37.5 mmol, washed with 3×10 mL hexanes) in anhydrous dimethyl formamide (200 mL) at room temperature. The resulting red solution was stirred for 20 minutes, then treated with dimethyl sulfate (4.33 g, 34.4 mmol)

which was added in one portion. The red color dissipated over 30 minutes to give a colorless mixture which was quenched by the addition of water. The mixture was extracted with $CH_2Cl_2$ (2×250 mL) and the combined organic layers were washed with water (2×250 mL), brine, dried over anhydrous sodium sulfate and concentrated in vacuo. The methyl ether, 2-tertiarybutyldimethylsilyloxymethyl-3-methoxy naphthalene, was obtained as a light yellow oil (8.94 g, 95%) of sufficient purity for use in the subsequent reaction.

The methoxy-silyl ether (8.9 g, 29.5 mmol) was vigorously stirred in 150 mL glacial acetic acid/water (2:1), for a total of 6 hours at room temperature. The mixture was extracted with $CH_2Cl_2$ (2×200 mL) and the combined organic layers were washed with water (2×200 mL), brine, dried over anhydrous sodium sulfate and concentrated in vacuo to give an oil. The oil was triturated with hexanes to give a white solid which was collected by filtration. More of the desired product was obtained from the filtrate by concentration in vacuo followed by chromatography on silica gel (Chromatotron 4 mm rotor), with elution by ethyl acetate/hexane (2:8) to give a total of 4.9 g (88%) of 3-methoxy-2-naphthalenylmethanol.

Carbon tetrabromide (9.50 g, 28.7 mmol), and triphenylphosphine (7.52 g, 28.7 mmol), were added to a stirred suspension of the alcohol produced in the preceding paragraph (4.9 g, 26.1 mmol) in 100 mL $CH_2Cl_2$ at 0° C. The mixture became a light yellow solution and was stirred at 0° C. for 15 minutes. The solvent was removed in vacuo and the remaining oil triturated with diethyl ether (200 mL) to give a precipitate. The solid was removed by filtration and the filtrate concentrated in vacuo.

Flash chromatography on silica gel with elution by ethyl acetate/hexane (1:9) gave the clean bromide, 2-bromomethyl-3-methoxynaphthalene (4.0 g, 61%), as a white crystalline solid.

KCN (1.23 g, 18.88 mmol) was added to a solution of the bromide prepared in the preceding paragraph (3.95 g, 15.7 mmol) in 125 mL of dimethylsulfoxide at room temperature. The resulting mixture was stirred for 1.5 hour, diluted with water (300 mL) and stirred another 15 minutes. The resulting precipitate was collected by filtration, washed with water and dried in vacuo to give the desired 2-(3-methoxynaphthalenyl)acetonitrile (2.50 g, 81%) of sufficient purity for use in the subsequent reaction.

Hydroxylamine hydrochloride (2.21 g, 31.7 mmol), was added in one portion to a solution of sodium methoxide, freshly prepared from sodium (0.73 g, 31.7 mmol) in methanol (100 mL). The resulting mixture was stirred for 1 hour at room temperature, during which time a precipitate formed. The nitrile prepared in the preceding paragraph (2.50 g, 12.7 mmol), was added in one portion and the resulting mixture was heated to reflux for 30 hours. The mixture was cooled to room temperature, and diluted with water (175 mL) to give a precipitate. The mixture was cooled to 0° C. for 10 minutes, the precipitate was collected by filtration, washed with water, and dried in vacuo to give a yellow solid (1.19 g) as a mixture of products.

The crude material was purified by chromatography on silica gel (Chromatotron 4 mm rotor), with elution by 1% methanol in $CHCl_3$ to give N'-hydroxy-(3-methoxy-2-naphthalenyl)ethanimidamide (0.080 g, 27%).

The amidoxime (0.8 g, 3.48 mmol) prepared in the preceding paragraph, was suspended in toluene (30 mL) and heated to 80° C. until all of the solid had dissolved. Thionyl chloride (2.26 mL, 2M in $CH_2Cl_2$, 4.52 mmol) was added dropwise to the above solution under a stream of nitrogen and a white precipitate was formed. The mixture was heated to reflux for 15 minutes, during which the precipitate dissolved to give an orange solution. The hot solution was filtered to remove trace solids and the filtrate was concentrated in vacuo to give the crude product.

The crude product was recrystallized from $CH_2Cl_2$ to give the title compound, m.p. 143°–145° C. (0.35 g, 36%).

Elemental analysis for $C_{13}H_{12}N_2O_3S$; Calc'd: C, 56.51; H, 4.38; N, 10.14; Found: C, 56.23; H, 4.62; N, 9.75;

Body weight increase over control: 120%.

EXAMPLE 7

4-[(6-Methoxy-3-naphthalenyl)methyl]-3H-1,2,3,5-oxathiadiazole-2-oxide

Following the procedure of Example 1, 6-methoxy-2-naphthalenyl acetonitrile (4.4 g, 0.022 mol) was added to a suspension of hydroxylamine HCl (2.8 g, 0.04 mol), sodium methoxide/MeOH 25% (9.43 mL, 0.04 mol) and MeOH (60 mL) and then brought to reflux for 3 hours. The reaction was then concentrated and ethyl acetate and $H_2O$ were added. The organic layer was separated, dried over $MgSO_4$ and concentrated in vacuo. Recrystallization of the crude solid from ethyl acetate afforded N'-hydroxy-(6-methoxy-2-naphthalenyl)ethanimidamide (2.4 g).

A suspension of the product of the preceding paragraph (2.24 g, 0.0097 mol), toluene (584 mL) and 2M thionyl chloride/$CH_2Cl_2$ (5.84 mL, 0.011 mol) was refluxed for 30 minutes. The solution was cooled quickly, filtered through Solka-floc, ® washed with saturated sodium chloride, and dried over $MgSO_4$. Upon concentration, a brown solid was obtained which was chromatographed on silica gel ($CH_2Cl_2CH_2Cl_2$/acetone). The title compound was obtained as a tan solid (0.96 g, yield 36%), m.p. 146°–147° C.

Elemental analysis for $C_{13}H_{12}N_2O_3S$; Calc'd: C, 56.51; H, 4.38; N, 10.14; Found: C, 56.67; H, 4.62; N, 9.94;

Body weight increase over control: 47%.

What is claimed is:

1. In an animal feed composition, the improvement which comprises incorporation of a growth promoting amount of a compound of the formula:

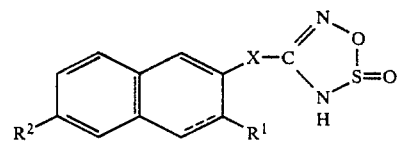

in which
the dotted line represents optional unsaturation;
$R^1$ is hydrogen, halo or alkoxy of 1 to 3 carbon atoms;
$R^2$ is hydrogen or alkoxy of 1 to 3 carbon atoms; and
X is methylene, ethylene, ethylidene, 1,2-propylene or propylene; or a biologically acceptable salt thereof.

2. An animal feed composition of claim 1 in which the growth promoting compound is 4-[(3,4-dihydro-2-naphthalenyl)methyl]-3H-1,2,3,5-oxathiadiazole-2-oxide.

3. An animal feed composition of claim 1 in which the growth promoting compound is 4-[1-(2-naphthalenyl)ethyl]-3H-1,2,3,5-oxathiadiazole-2-oxide.

4. An animal feed composition of claim 1 in which the growth promoting compound is 4-[1-methyl-2-(2-naphthalenyl)ethyl]-3H-1,2,3,5-oxathiadiazole-2-oxide.

5. An animal feed composition of claim 1 in which the growth promoting compound is 4-[3-(2-naphthalenyl)propyl]-3H-1,2,3,5-oxathiadiazole-2-oxide.

6. An animal feed composition of claim 1 in which the growth promoting compound is 4-[(3-bromo-2-naphthalenyl)methyl]-3H-1,2,3,5-oxathiadiazole.

7. An animal feed composition of claim 1 in which the growth promoting compound is 4-[(3-methoxy-2-naphthalenyl)methyl]-3H-1,2,3,5-oxathiadiazole-2-oxide.

8. An animal feed composition of claim 1 in which the growth promoting compound is 4-[(6-methoxy-3-naphthalenyl)methyl]-3H-1,2,3,5-oxathiadiazole-2-oxide.

9. A process for rapidly increasing the lean body mass of a ruminant or monogastric mammal which comprises feeding said mammal a growth promoting quantity of a compound of the formula:

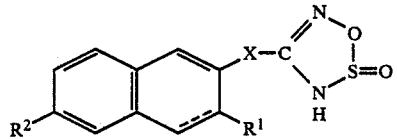

in which
the dotted line represents optional unsaturation;
R¹ is hydrogen, halo or alkoxy of 1 to 3 carbon atoms;
R² is hydrogen or alkoxy of 1 to 3 carbon atoms and
X is methylene, ethylene, ethylidene, 1,2-propylene or propylene; or a biologically acceptable salt thereof.

10. A process for increasing proteinaceous body mass in a mammal which comprises orally administering to a patient in need thereof a growth promoting amount of a compound of the formula:

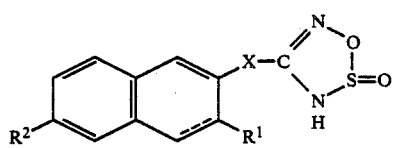

in which
the dotted line represents optional unsaturation;
R¹ is hydrogen, halo or alkoxy of 1 to 3 carbon atoms;
R² is hydrogen or alkoxy of 1 to 3 carbon atoms and
X is methylene, ethylene, ethylidene, 1,2-propylene or propylene; or a biologically acceptable salt thereof.

* * * * *